United States Patent [19]

Hinman, Jr.

[11] 4,126,135
[45] Nov. 21, 1978

[54] SELF-STANDING COLLAPSIBLE URINARY DRAINAGE BAG

[76] Inventor: Frank Hinman, Jr., 1000 Francisco St., San Francisco, Calif. 94109

[21] Appl. No.: 755,621

[22] Filed: Dec. 30, 1976

[51] Int. Cl.² .................................................. A61F 5/44
[52] U.S. Cl. .................................................. 128/275
[58] Field of Search .............. 128/275, 272, 226, 227, 128/228, DIG. 24; 222/105, 107, 103, 214, 215; 229/55, 31, 14 B, 14 BL, 14 BW; 215/DIG. 3, 11, 99, 100, 307, 321, 354; 248/311, 312, 313, 97; 206/499, 503, 594, 583; 150/1.05, 8, 48–51

[56] References Cited

U.S. PATENT DOCUMENTS

| 302,862 | 7/1894 | Ott | 401/152 |
| 1,389,772 | 9/1921 | Miller | 401/158 |
| 2,915,222 | 12/1959 | Purington | 128/226 |
| 3,211,144 | 10/1965 | Nehring | 128/214 D |
| 3,263,848 | 8/1966 | Zackheim | 128/DIG. 24 |
| 3,319,684 | 5/1967 | Calhoun | 128/275 |
| 3,339,721 | 9/1967 | Goldstein | 206/583 |
| 3,872,868 | 3/1975 | Kline | 128/DIG. 24 |

*Primary Examiner*—Robert W. Michell
*Assistant Examiner*—Arthur S. Rose
*Attorney, Agent, or Firm*—Naylor, Neal & Uilkema

[57] ABSTRACT

A self-standing urinary bag structure comprising a pair of generally rigid leaves hingedly secured together at the apical portions thereof and having a bag suspended therebetween. The bag is so positioned as to extend partially beneath the leaves when the structure is suspended from above and to force the leaves apart into a self-standing condition when the structure is placed upon a support surface disposed therebeneath. In one embodiment the leaves are integrally joined to the bag and in another embodiment the leaves are removable from the bag.

6 Claims, 12 Drawing Figures

SELF-STANDING COLLAPSIBLE URINARY DRAINAGE BAG

BACKGROUND OF THE INVENTION

The present invention relates to flexible urinary drainage bags and, particularly, to an improved bag and support structure which is self-standing and will maintain the inlet system for the bag in an elevated condition when the bag is rested upon a support surface, such as the floor.

Rigid urinary drainage bags capable of standing alone are known in the prior art, but have been largely abandoned because they do not accommodate to carriage under patients' clothing, nor to bedside hanging. Flexible urinary drainage bags of the type presently in use are well facilitated for carriage under patients' clothing or hanging from a bed, but are not adapted to be self-standing when placed on a support surface, such as the floor. Such placement generally occurs when a patient sits in a bedside chair and occurs, almost without exception, when a patient using such a bag defecates in the toilet. It results in the bag lying on its side so that the inlet system for the bag is flooded with the contained urine, which may already be contaminated. Where the urine is contaminated, flooding of the inlet system generally results in ascent of bacteria to the bladder and in resulting infection.

U.S. Pat. Nos. 3,186,410; 3,299,422; and 3,357,429 exemplify flexible urinary drainage bags of the type well known in the prior art. These bags are not self-standing in the sense of the bag forming the subject of the present invention. U.S. Pat. No. 3,263,848 discloses a flexible nursing container which is relevant in that it is provided with a framing structure adapted to support the container in an upright condition. The framing structure, however, is materially different from that of the present invention in both structure and mode of operation. U.S. Pat. No. 3,339,721 discloses a flexible bag supported in a self-standing structure which is similar to that of the present invention in that the structure includes hingedly interconnected side panels between which the bag is suspended. The bag is not, however, adapted to hang beneath the panels so that, upon placing the structure on a support surface, the bag forces the panels apart into a self-standing condition.

SUMMARY OF THE INVENTION

In its broadest aspects, the device of the present invention comprises two semi-rigid panels or frames which are hingedly secured together at the apical portions and between which a urinary drainage bag is suspended. The bag is so positioned that when the device is set down, the bag spreads and pushes the panels apart to form a generally rectangular support base. When the device is suspended from above, the bag and the side panels collapse inwardly to permit the device to conform to any supporting structure, such as a bed railing, or to a patient's clothing.

DESCRIPTION OF THE ILLUSTRATED EMBODIMENTS

Figure 1:
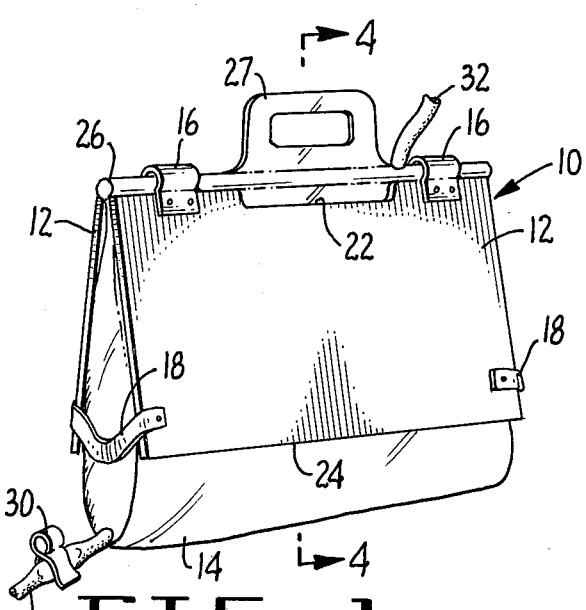
FIG. 1 is a perspective view of a first embodiment structure of the invention wherein a removable adapter is provided to make the bag self-standing, illustrating the structure as it would appear when suspended and in an empty condition.
Figure 2:
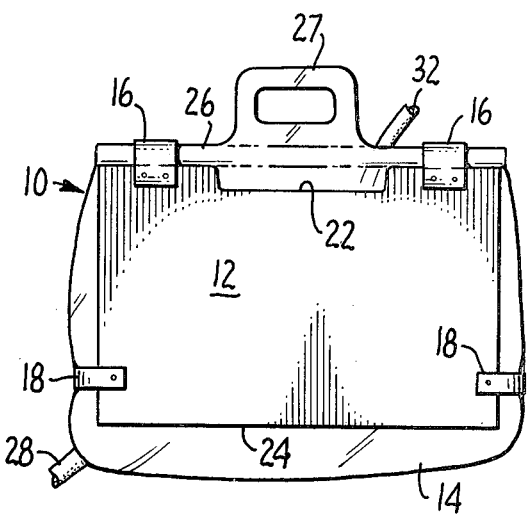
FIG. 2 is a side elevational view of the first embodiment structure, illustrating the structure as it would appear when suspended in an empty condition.
Figure 3:
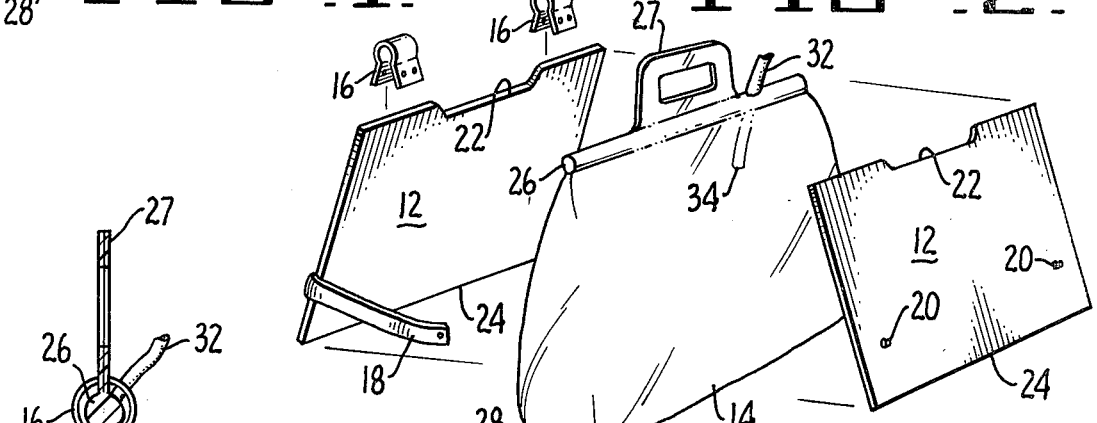
FIG. 3 is an exploded perspective view of the first embodiment structure.
Figure 4:
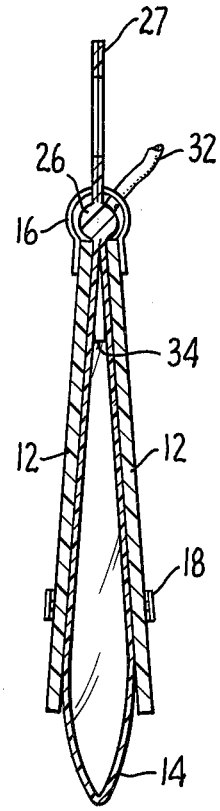
FIG. 4 is a cross-sectional elevational view taken on the plane designated by Line 4—4 of FIG. 1.

The first embodiment structure is designated in its entirety by the numeral 10 and comprises, as its basic elements, a pair of generally rigid leaves 12 having a flexible urine bag 14 suspended therebetween. The leaves may be fabricated of any suitable material, such as rigid polyethylene, and are hingedly secured together at the apical portions thereof by spring hinges 16. The hinges 16 are disposed to normally bias the leaves toward one another into the generally juxtaposed condition illustrated in FIGS. 1 and 4. Each hinge comprises a leaf spring element of generally inverted U-shaped configuration having the legs thereof secured to the outer surfaces of the leaves, as by riveting. Straps 18 are secured between the leaves 12 to limit the extent to which the leaves can spread. The straps 18 are flexible and, in the preferred embodiment, fixedly connected at one end to one of the leaves and removably connected at the other end to the other of the leaves. FIG. 3 illustrates snaps 20 which may be used to provide the removable connection.

The upper ends of the leaves 12 are provided with excised portions 22 to provide for the extension of a bag handle therethrough. The lower ends of the leaves 12 provide straight edges 24 which serve as the feet of the structure when the structure is put to rest on a support surface, as illustrated in FIG. 6.

The bag 14 is fabricated of a flexible material, such as soft polyvinylchloride, and has an upper bead 26 and handle 27 formed integrally therewith. At its lower end, the bag is provided with a discharge conduit 28 having a removable clamp 30 secured thereto. The upper end of the bag is provided with an inlet system in the form of an inlet conduit 32 sealingly engaged within an opening provided therefor in the bag. The distal end of the inlet conduit, designated 34, is disposed so as to be suspended within the upper portion of the bag out of contact with the walls of the bag.

The bead 26 is so proportioned relative to the space between the upper edges of the leaves 12 that the bead may be passed through this space when the straps 18 are disconnected and the leaves are manually spread apart beyond the limited degree of spreading permitted when the straps are connected between the leaves. The proportioning of the bead relative to the distance between the upper edges of the leaves is also such that the bead will maintain the bag in the suspended condition illustrated in FIGS. 1, 2, 4, 5 and 6, so long as the spreading of the leaves is limited by the connection of the straps 18 between the leaves. Thus, it will be appreciated that the bag 14 is normally suspended between the leaves by the bead 26 and that the bag may be selectively released and replaced by disconnecting the straps 18 and spreading the leaves.

Figure 5:
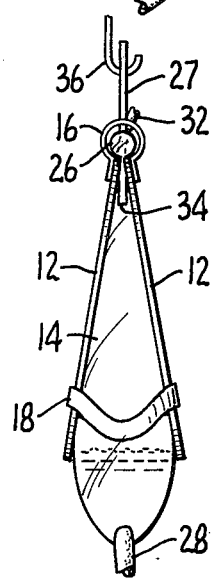
FIG. 5 is an end elevational view of the first embodiment structure, as it would appear when suspended from above, with the urine contained in the bag.
Figure 6:
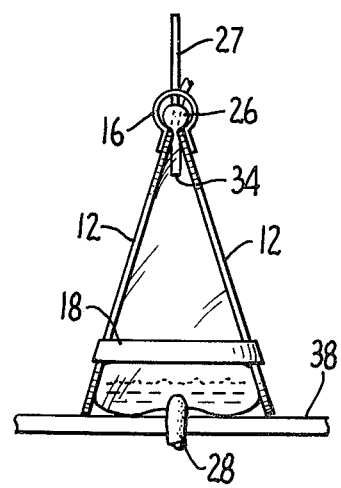
FIG. 6 is an end elevational view of the first embodiment structure, as it would appear when supported from beneath on a support surface, with urine contained in the bag.
Figure 7:
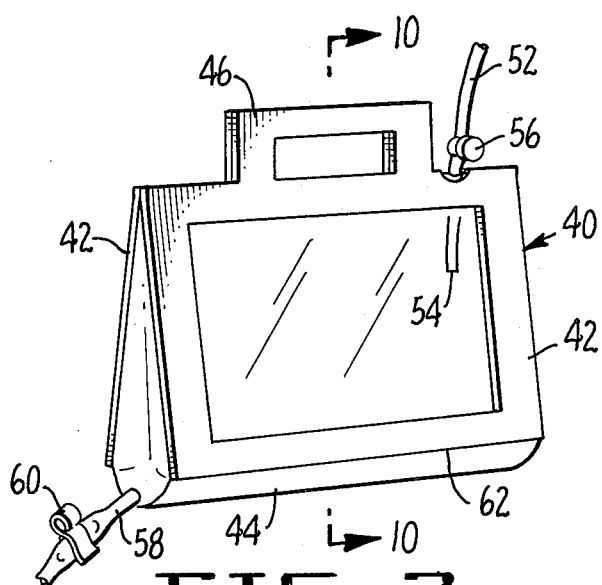
FIG. 7 is a perspective view of a second embodiment structure of the present invention wherein the self-supporting structure is integrally joined to the bag, illustrating the structure as it would appear when suspended from above with the bag in an empty condition.

In use, the first embodiment structure normally assumes either the condition illustrated in FIG. 5 or that illustrated in FIG. 6. FIG. 5 shows the structure as it would appear when suspended from above to the frame of a bed or other similar support by a hook 36. FIG. 6 shows the structure as it would appear when supported from beneath on a support surface 38, such as the floor. From a comparison of FIGS. 5 and 6, it will be seen that the bag 14 hangs beneath the leaves 12 when the structure is suspended from above and that, when the structure is supported from below, the bag and the urine contained therein function to spread the leaves 12 apart into the self-supporting condition illustrated in FIG. 6. In both the FIG. 5 condition and the FIG. 6 condition, the distal end 34 of the inlet conduit is maintained in an elevated condition out of contact with the bag and any urine contained in the lower portion of the bag. Thus, the conduit is isolated from possible contamination by urine contained within the bag.

The second embodiment structure of FIGS. 7 to 12 is designated in its entirety by the numeral 40 and comprises, as its basic elements, a pair of semi-rigid frame elements or leaves 42 hingedly secured together at their apical portions and having suspended therebetween a flexible bag 44. The frame elements 42 may be fabricated of any suitable material, such as semi-rigid polyethylene. In the preferred arrangement illustrated, the elements are welded together at their apical portions and hinging is provided by flexibility of the material from which the elements are fabricated. A handle 46 is integrally formed with the frame elements.

Figure 9:
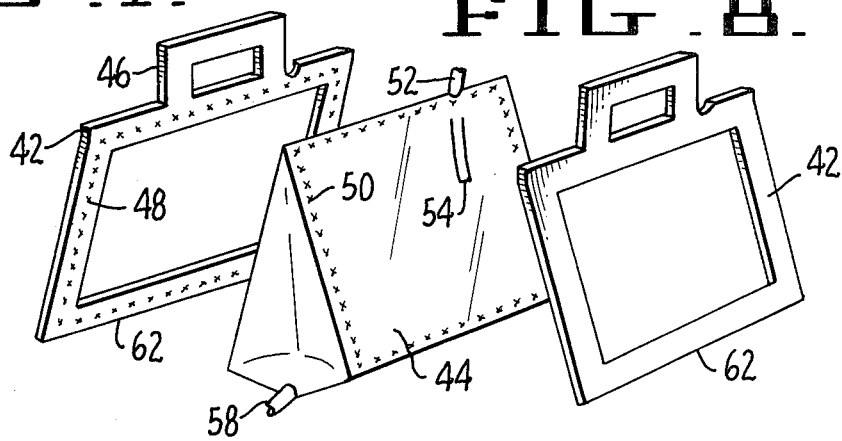
FIG. 9 is an exploded perspective view of the second embodiment structure.
Figure 10:
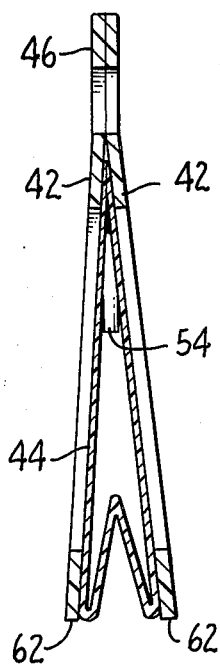
FIG. 10 is a cross-sectional elevational view of the second embodiment structure, taken on the plane designated by Line 10—10 of FIG. 7.

The bag 44 is formed of a flexible material, such as soft polyvinylchloride, and is welded to the inside sides of the frame elements 42 so as to be suspended therebetween. In the preferred embodiment illustrated, the welds between the bag and the frame elements extend around the entire periphery of the frame elements. The weld lines are depicted in FIG. 9 and designated by the numerals 48 and 50. From FIG. 9, it will also be seen that the end and side walls of the bag 44 are of sufficient length to permit the frame elements 42 to hingedly move relative to one another between the contracted condition illustrated in FIG. 10 and the expanded condition illustrated in FIG. 12.

The inlet system for the second embodiment structure comprises an inlet conduit 52 sealingly secured in an opening in the upper end of the bag and extending partially into the bag to provide a distal end 54 spaced from the walls and the bottom of the bag. In the embodiment illustrated, a valve 56 is provided in the conduit 52. The drainage system for the bag 44 comprises a conduit 58 sealingly connected to the bag and extending into fluid communication with its lower portion. A removable clamp 60 is provided to normally maintain the conduit 58 in a closed condition.

Figure 8:
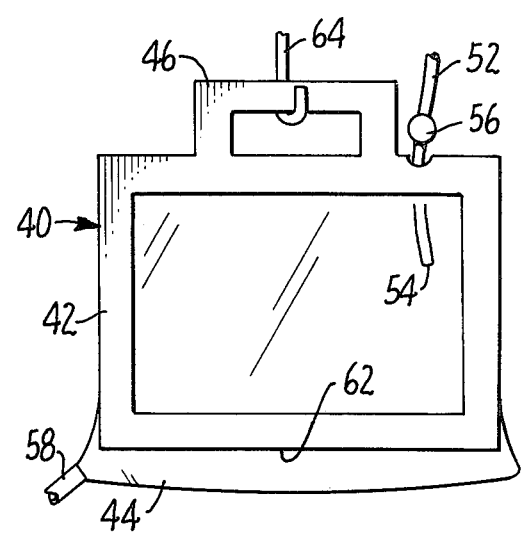
FIG. 8 is a side elevational view of the second embodiment structure, illustrating the structure as it would appear when suspended from above with the bag in an empty condition.
Figure 11:
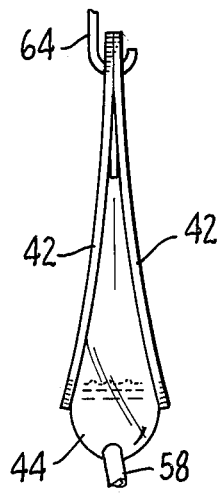
FIG. 11 is an end elevational view, illustrating the second embodiment structure as it would appear when suspended from above with urine contained in the bag; and, FIG. 12 is an end elevation view, illustrating the second embodiment structure as it would appear when supported from beneath on a support surface, with urine contained in the bag.
Figure 12:
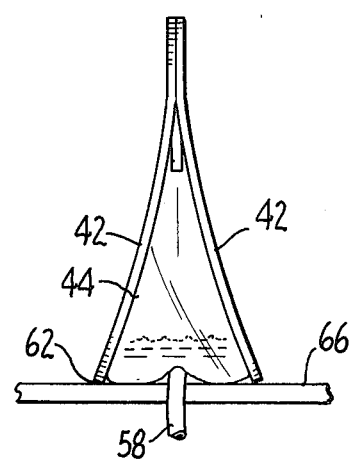

In use, the second embodiment structure operates in essentially the same manner as the first embodiment structure, with the exception that the bag of the second embodiment structure is not removable from the leaf-like frame elements. Similarly to the first embodiment structure, the lower extremities of the frame elements 42 define straight edges 62 which function as feet for the structure when it is rested upon a support surface, as illustrated in FIG. 12. The suspended condition of the structure 40 is illustrated in FIGS. 8 and 11 wherein the structure is shown suspended by a hook 64 extending through the handle 46. FIG. 11 graphically illustrates that, when suspended from above with urine contained within the bag, the bottom of the bag hangs beneath the lower edges of the frame elements 42. FIG. 12 illustrates that the urine contained within the bag functions to spread the frame elements when the structure is rested upon a support surface disposed therebeneath. The support surface in FIG. 12 is designated by the numeral 66.

CONCLUSION

From the foregoing detailed description, it should be apparent that the present invention provides a collapsible bag which assues that the inlet system for the bag is maintained in an elevated condition, whether the bag is suspended from above or supported from below. It should be understood, however, that the invention is not intended to be limited to the specifics of the illustrated embodiments, but rather is defined by the accompanying claims.

What is claimed is:

1. A self-standing urinary bag structure comprising: a pair of generally rigid leaves hingedly secured together at the apical edges thereof for movement into a collapsed condition wherein the leaves are disposed in face-to-face, generally juxtaposed, relationship to one another and an extended condition wherein the bottom portions of the leaves are spread relative to one another to provide a self-standing structure; a flexible bag suspended between said leaves by welded connections to the top, side and bottom portions thereof and having sufficient breadth between said connections to enable said leaves to spread to the extended condition and said bag to extend partially beneath said leaves when the leaves are suspended from above; and, inlet conduit means secured to the bag and suspended within an upper portion thereof to provide for the conduct of urine into the bag.

2. A structure, according to claim 1, wherein a handle is secured to the apical edges of the leaves.

3. A self-standing urinary bag structure comprising: a pair of generally rigid leaves hingedly secured together at the apical edges thereof for movement into a collapsed condition wherein the leaves are disposed in face-to-face, generally juxtaposed, relationship to one another and an extended condition wherein the lower edges of the leaves are spread relative to one another to provide a self-standing structure; a flexible bag suspended between said leaves by welded connections to the top and bottom portions thereof, said bag having a flexible segment spanning the space between the connections to the bottom portions of the leaves of such a length that it hangs beneath the leaves when the leaves are suspended from above and permits the leaves to spread apart when the structure is placed on a support surface disposed therebeneath; and, inlet conduit means secured to the bag and suspended within an upper portion thereof to provide for the conduct of urine into the bag.

4. A self-standing urinary bag structure comprising: a pair of generally rigid leaves hingedly secured together at the apical edges thereof by spring biased hinges for movement into a collapsed condition wherein the leaves are disposed in face-to-face, generally juxtaposed, relationship to one another and an extended condition wherein the lower edges of the leaves are spread relative to one another to provide a self-standing structure, said hinges normally biasing the leaves toward the collapsed condition and being so disposed that the apical edges of the leaves spread upon forcing of the leaves apart; a flexible bag suspended between said leaves by a bead formed integrally with the bag at the upper portion thereof and supported on the apical edges of the leaves, said bead being adapted to be passed between the apical edges of the leaves upon forcing the leaves apart to a predetermined degree exceeding the degree to which the leaves are spread when disposed in the extended condition wherein the structure is self-standing, said bag having sufficient breadth to extend partially beneath said leaves when the leaves are suspended from above and to force the lower edges of the leaves apart when the structure is placed upon a support surface disposed therebeneath; and, inlet conduit means secured to the bag and suspended within an upper portion thereof to provide for the conduit of urine into the bag.

5. An adapter for supporting a flexible urinary bag, said adapter comprising: a pair of generally rigid leaves; spring biased hinges securing said leaves together at the apical edges thereof for movement between a collapsed condition wherein the leaves are disposed in face-to-face, generally juxtaposed, relationship to one another and an extended condition wherein the lower edges of the leaves are spread relative to one another to provide a self-standing structure, said hinges normally biasing the leaves toward the collapsed condition and being so disposed that the apical edges of the leaves spread upon forcing of the leaves apart; portions on said apical edges of the leaves to releasably secure a flexible urinary bag to said adapter in a position suspended between said leaves wherein, when the leaves are suspended from above, the bag projects partially beneath the lower extremities of the leaves.

6. An adapter, according to claim 5, further comprising means to limit the extent to which said leaves may spread when in the extended condition.

* * * * *